United States Patent [19]

Weinberger

[11] Plant 4,965

[45] Dec. 14, 1982

[54] PLUM TREE

[75] Inventor: John H. Weinberger, Fresno, Calif.

[73] Assignee: Superior Farming Company, Bakersfield, Calif.

[21] Appl. No.: 293,301

[22] Filed: Aug. 17, 1981

[51] Int. Cl.[3] ..... A01H 5/03

[52] U.S. Cl. ..... Plt./38

[58] Field of Search ..... Plt./38

*Primary Examiner*—Robert E. Bagwill

*Attorney, Agent, or Firm*—Roger B. Webster

[57] ABSTRACT

A plum tree which is of medium size, medium vigor, spreading, dense, and round-topped; foliated with medium size, obovate, medium pointed, medium thick, smooth-textured leaves having a crenate margin, a petiole medium in length and thickness, and small, irregularly opposite, globose glands; flowers from pointed, free buds of medium size and length; the flowers, of medium season, being medium size and white; and is a regular and very productive bearer of medium size, uniform, symmetrical, globose, semi-freestone fruit having dark purple skin, red flesh, and a brownish-yellow stone.

1 Drawing Figure

BACKGROUND OF THE VARIETY

1. Field of the Invention

In the conduct of an extensive plant breeding program—on behalf of a commercial farming company, and in such company's experimental orchard located near Fresno, Fresno County, Calif.—I have originated a substantial number of new and distinct varieties of fruit trees, and which include the present variety of plum tree.

2. Classification of the Variety

The present variety of plum tree is embraced by Class 38, Plants, of the U.S. Patent Office MANUAL OF CLASSIFICATION.

3. Prior Varieties

Among existing varieties of plum trees which are known to me, and mentioned herein, are the Eldorado (unpatented) and the Angeleno (U.S. Plant Pat. No. 2,747).

ORIGIN OF THE VARIETY

The present variety of plum tree was originated by me as an open pollinated seedling of the Angeleno plum tree. A number of such seedlings were grown to fruition, in the aforesaid experimental orchard, under careful and continuing observation by me; the present variety being a selection from such seedlings which evidenced commercial promise.

ASEXUAL REPRODUCTION OF THE VARIETY

Asexual reproduction of the variety was successfully accomplished, under my direction and in the aforesaid experimental orchard, by budding; such asexual reproductions, in maturity, having run true to the original tree in all respects.

SUMMARY OF THE VARIETY

The present variety of plum tree is, characteristically, of medium size, medium vigor, spreading, dense, and round-topped; foliated with medium size, obovate, medium pointed, medium thick, smooth-textured leaves having a crenate margin, a petiole medium in length and thickness, and small, irregularly opposite, globose glands; flowers from pointed, free buds of medium size and length; the flowers, of medium season, being medium size and white; and is a regular and very productive bearer of medium size, uniform, symmetrical, globose, semi-freestone fruit having dark purple skin, red flesh, and a brownish-yellow stone.

The present variety of plum tree is further characterized by semi-freestone fruit having red flesh in a season when nearly all other varieties of plum trees bear fruit having yellow flesh. Associated with the red flesh is relatively low acidity which enhances the fruit quality.

The present variety of plum tree is still further characterized by semi-freestone fruit which ripens about with the fruit of the Eldorado, and which it most nearly resembles, but, in comparative distinction, the globose fruit of the present variety has red flesh rather than the yellow flesh of the oblate fruit of the Eldorado.

BRIEF DESCRIPTION OF THE DRAWING

The drawing is an illustration, by photographic reproduction in color, of a twig with leaves, and separate fruit; one fruit being cut in half to expose the flesh, and the stone remaining in one of the halves.

DESCRIPTION OF THE VARIETY

The botanical details of this new and distinct variety of plum tree—with color definitions (except those in common color terms) referenced to Plochere Color System (in book form)—are as follows:

Tree:
- *Size.*—Medium.
- *Vigor.*—Medium.
- *Growth.*—Spreading.
- *Density.*—Dense.
- *Form.*—Round-topped.
- *Production.*—Very productive.
- *Bearing.*—Regular bearer.

Trunk:
- *Size.* —Medium.
- *Texture.*—Medium.

Branches:
- *Size.*—Medium.
- *Texture.*—Medium.
- *Color.*—New wood: Green. Mature wood: Brown.

Leaves:

*Size.*—Medium. Average length — 10.6 cm. Average width — 4.6 cm.
*Form.*—Obovate. Medium Pointed.
*Thickness.*—Medium.
*Color.*—Medium green.
*Texture.*—Smooth.
*Margin.*—Crenate.
*Petiole.*—Medium length. Medium thickness.
*Glands.*—Average number — 4. Irregularly opposite. Small. Globose. Green. Positioned distal on petiole, a few basal on blade.
*Stipules.*—Occasional.

Flower buds:
*Size.*—Medium.
*Length.*—Medium.
*Form.*—Pointed. Free.

Flowers:
*Date of full bloom.*—Feb. 28, 1980. Medium, as compared with other varieties.
*Size.*—Medium.
*Color.*—White.

Fruit:
*Maturity when described.*—Firm ripe — July 1, 1980.
*Date of first picking.*—June 30, 1980.
*Date of last picking.*—July 8, 1980.
*Size.*—Medium. Average diameter axially — 61 mm. Average transversely in suture plane — 61 mm.
*Form.*—Uniform. Symmetrical. Globose.
*Suture.*—A shallow, inconspicuous line extending from base to apex, with slight depression beyond pistil point.
*Ventral surface.*—Rounded. Lipped on both sides.
*Lips.*—Equal.
*Cavity.*—Rounded. Elongated in suture plane on both sides. Average depth — 10 mm. Average breadth — 13 mm. Markings — none.
*Base.*—Rounded.
*Apex.*—Short. Rounded.
*Pistil point.*—Apical.

Skin:
*Thickness.*—Medium.
*Texture.*—Medium.
*Tenacity.*—Tenacious to flesh.
*Tendency to crack.*—None in wet-dry seasons.
*Color.*—Dark purple (Plate 22 — No. 505 — Egg Plant).
*Down.*—Wanting.

Flesh:
*Color.*—Blood with greenish-reddish tinge (Plate 17 — No. 385 — Crimson Glory) streaked with red next to skin.
*Surface of pit cavity.*—Greenish brown.
*Amygdalin.*—Wanting.
*Juice.*—Moderate.
*Texture.*—Medium. Fine. Crisp.
*Fibers.*—Few. Fine. Tender.
*Ripens.*—Evenly.
*Flavor.*—Acid. Delicate.
*Aroma.*—Distinct.
*Eating quality.*—Good.

Stone:
*Type.*—Semi-free. Retains short fiber-like threads along edges.
*Size.*—Medium. Average length — 18 mm. Average Breadth — 15 mm. Average thickness — 9 mm.
*Form.*—Elliptical. Cuneate toward base.
*Base.*—Straight.
*Hilum.*—Oval.
*Apex.*—Acuminate.
*Sides.*—Equal.
*Surface.*—Ridged throughout.
*Ridges.*—Jagged throughout. Interrupted.
*Ventral edge.*—Thin, without wing.
*Dorsal edge.*—Full, with deep groove throughout.
*Color.*—Light brown (Plate 8 — No. 171 — French yellow).
*Tendency to split.*—Slight in dry season.

Use: Market.
Keeping quality: Good.
Shipping quality: Good.

The plum tree and its fruit herein described may vary in slight detail due to climatic and soil conditions under which the variety may be grown; the present description being of the variety as grown in the Central Valley of California.

I claim:

1. A new and distinct variety of plum tree, substantially as illustrated and described, particularly characterized by the regular and very productive bearing of semi-freestone fruit which ripens about with, and most nearly resembles, the fruit of the Eldorado, but, in comparative distinction, the globose fruit of the present variety has red flesh, whereas the oblate fruit of the Eldorado has yellow flesh.

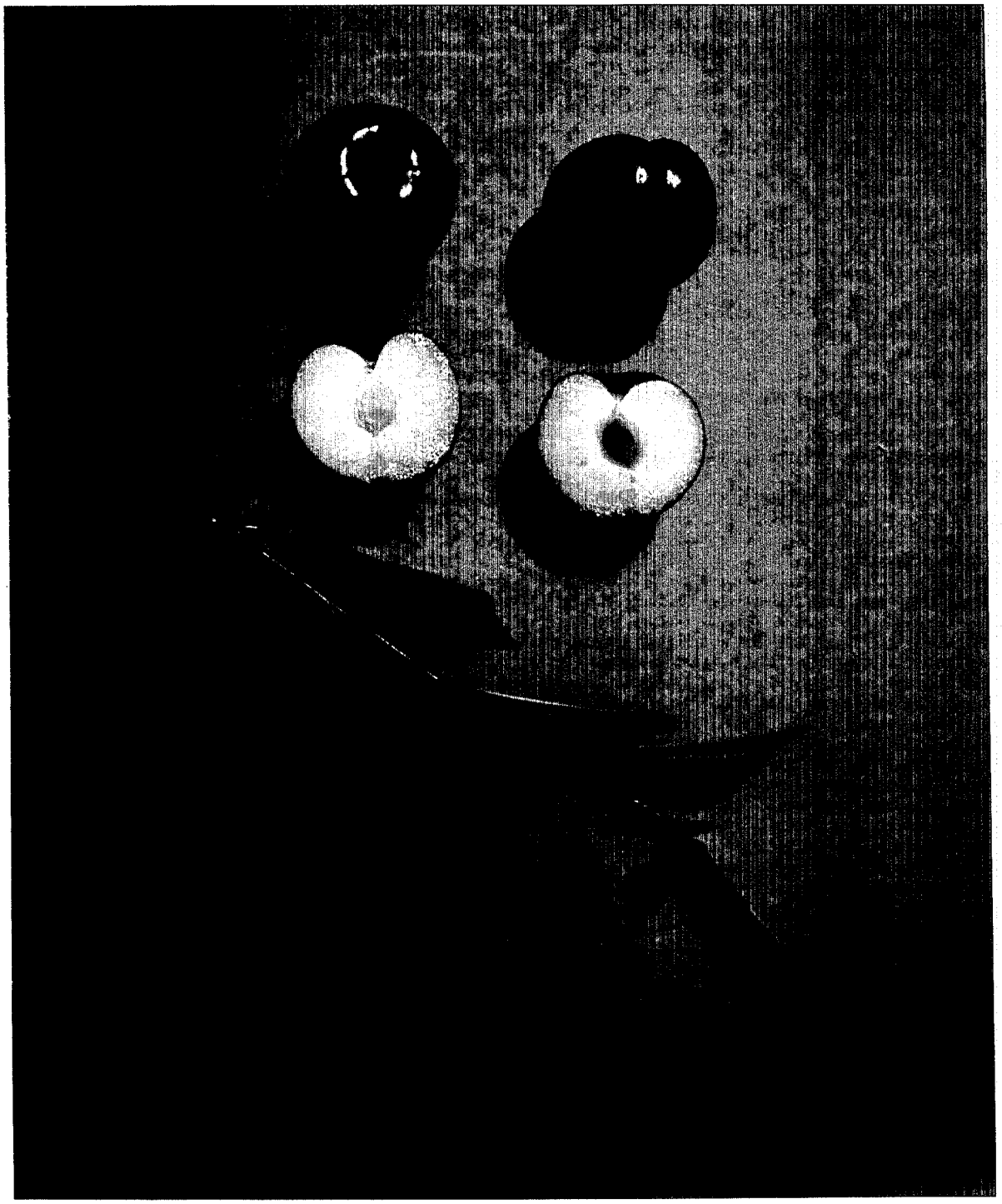

* * * * *